United States Patent [19]

Cummings et al.

[11] Patent Number: 4,956,145

[45] Date of Patent: Sep. 11, 1990

[54] OPTIMUM HYDROGEN PEROXIDE VAPOR STERILIZATION METHOD

[75] Inventors: Arthur L. Cummings; Robert W. Childers, both of Erie, Pa.

[73] Assignee: American Sterilizer Company, Erie, Pa.

[21] Appl. No.: 139,900

[22] Filed: Dec. 30, 1987

[51] Int. Cl.$^5$ .............................................. A61L 2/20
[52] U.S. Cl. ...................................... 422/28; 422/29; 422/33; 422/111
[58] Field of Search ...................... 422/28, 29, 33, 111

[56] References Cited

U.S. PATENT DOCUMENTS

| | | | |
|---|---|---|---|
| 4,169,123 | 9/1979 | Moore et al. | 422/28 X |
| 4,169,124 | 9/1979 | Forstrom et al. | 422/28 X |
| 4,642,165 | 2/1987 | Bier | 422/28 X |
| 4,687,635 | 8/1987 | Kaehler | 422/26 |
| 4,744,951 | 5/1988 | Cummings et al. | 422/28 |
| 4,756,882 | 7/1988 | Jacobs et al. | 422/28 X |

Primary Examiner—Robert J. Warden
Assistant Examiner—Jill Johnston
Attorney, Agent, or Firm—Kirkpatrick & Lockhart

[57] ABSTRACT

A sterilization method including the steps of injecting a hydrogen peroxide and water vapor mixture into a closed sterilization chamber of a predetermined volume at a predetermined temperature in an initial amount up to the saturation limit of such vapor mixture and thereafter, injecting a plurality of intermittent make-up injections of such vapor mixture into the chamber. The rate of the make-up injections and the amount of each such make-up injection is based on the rate and amounts necessary to maintain the concentration of hydrogen peroxide vapor at a level effective for sterilization but less than that which would raise the concentration of the vapor mixture to the saturation limit which will be present in the chamber immediately following injection of a make-up injection.

5 Claims, 6 Drawing Sheets

Pressure torr
Vapor % saturation
Relative Humidity %
Water mg/L
$H_2O_2$ mg/L

OPTIMUM HYDROGEN PEROXIDE VAPOR STERILIZATION METHOD

BACKGROUND OF THE INVENTION

1. Field of the Invention

The present invention relates to methods of sterilization, and more particularly, to a method of vapor phase hydrogen peroxide sterilization.

2. Description of the Prior Art

In 1979 Moore et al. disclosed in U.S. Pat. No. 4,169,123 a method of sterilizing with "cold" hydrogen peroxide vapor. Forstrom et al. U.S. Pat. No. 4,169,124 disclosed a similar method wherein the concentration of the hydrogen peroxide vapor is less than 75 mg/L. Bier U.S. Pat. No. 4,642,165 discloses a method of vaporizing multicomponent liquids such as hydrogen peroxide and water, and passing the vapor in successive small increments into a sterilization chamber.

Hydrogen peroxide is rarely, if ever, used in a pure form. It is typically mixed with water. Hydrogen peroxide vapor, like water vapor, is a condensable gas, but is less volatile than water vapor. When injected into a sterilizer with water vapor, the hydrogen peroxide vapor may readily decompose into water and oxygen or condense into liquid. Thus, the concentration of vapor phase hydrogen peroxide within a sterilization chamber will decrease with time as degradation and/or condensation occurs.

It is necessary in order to achieve effective sterilization, to maintain the concentration of the sterilant at effective levels throughout the sterilization phase of a cycle. The Bier patent referenced above discloses that the multicomponent vapor should be introduced in successive increments but it does not address the question of the degradation of the hydrogen peroxide vapor after injection into the sterilization chamber or the problems of exceeding the saturation limit of the vapor mixture.

One problem with indiscriminate successive injections of a hydrogen peroxide and water vapor mixture into the sterilization chamber is that the concentrations of the condensable vapors can exceed the saturation limit of the mixture causing the vapors to condense. The saturation limit generally increases with increasing temperature and varies with the relative concentrations of the different molecular species of the mixture. When the mixture is comprised of hydrogen peroxide and water the problem is compounded because of the degradation of hydrogen peroxide into water and oxygen. The increase in water vapor concentration resulting from such degradation reduces the saturation limit of the mixture and accordingly, reduces the maximum hydrogen peroxide vapor concentration that can be injected into the chamber without causing the vapor mixture to condense.

It is an object of the present invention to provide a vapor phase hydrogen peroxide sterilization method wherein the problems of exceeding the saturation limit of the vapor mixture and the degradation of hydrogen peroxide vapor to water vapor and oxygen are overcome. It is a further object of the present invention to provide an optimum vapor phase hydrogen peroxide sterilization method in order to ensure that an effective level of hydrogen peroxide vapor is present throughout the sterilization stage of the cycle.

SUMMARY OF THE INVENTION

The present invention provides an optimum hydrogen peroxide vapor sterilization method. The method succeeds in maintaining an effective level of hydrogen peroxide vapor in the sterilization chamber to ensure effective sterilization. The method includes the steps of injecting a hydrogen peroxide and water vapor mixture into a sterilization chamber having a predetermined volume at a predetermined temperature in an initial amount less than the saturation limit of the vapor mixture in the chamber at such temperature and such volume and thereafter, injecting a plurality of intermittent make-up injections of the vapor mixture into the chamber, the make-up injections being at a rate and each such make-up injection being in a variable amount necessary to maintain the concentration of hydrogen peroxide vapor at a level effective for sterilization but less than that concentration of hydrogen peroxide vapor which would raise the concentration of the vapor mixture to the saturation limit which will be present in the chamber immediately following injection of such make-up injection at such temperature.

The hydrogen peroxide and water vapor mixture is preferably a 30% by weight composition at about 4° C. The saturation limits and the initial and variable amounts of the vapor mixture may be determined by continuously monitoring the hydrogen peroxide vapor concentration and the water vapor concentration within the chamber. Alternatively, the saturation limits and the initial and variable amounts of the vapor mixture may be predetermined according to the procedures set forth in more detail hereinbelow.

BRIEF DESCRIPTION OF THE FIGURES

The present invention can be better understood by reference to the figures in which.

DETAILED DESCRIPTION OF THE PREFERRED EMBODIMENT

The optimum hydrogen peroxide vapor sterilization cycle of the present invention is illustrated graphically in FIGS. 1 through 4. For comparison, and to illustrate the advantages of the optimum sterilization cycle of the present invention, the consequences of two other hydrogen peroxide vapor sterilization cycles are illustrated in FIGS. 5 through 11.

Figure 5:
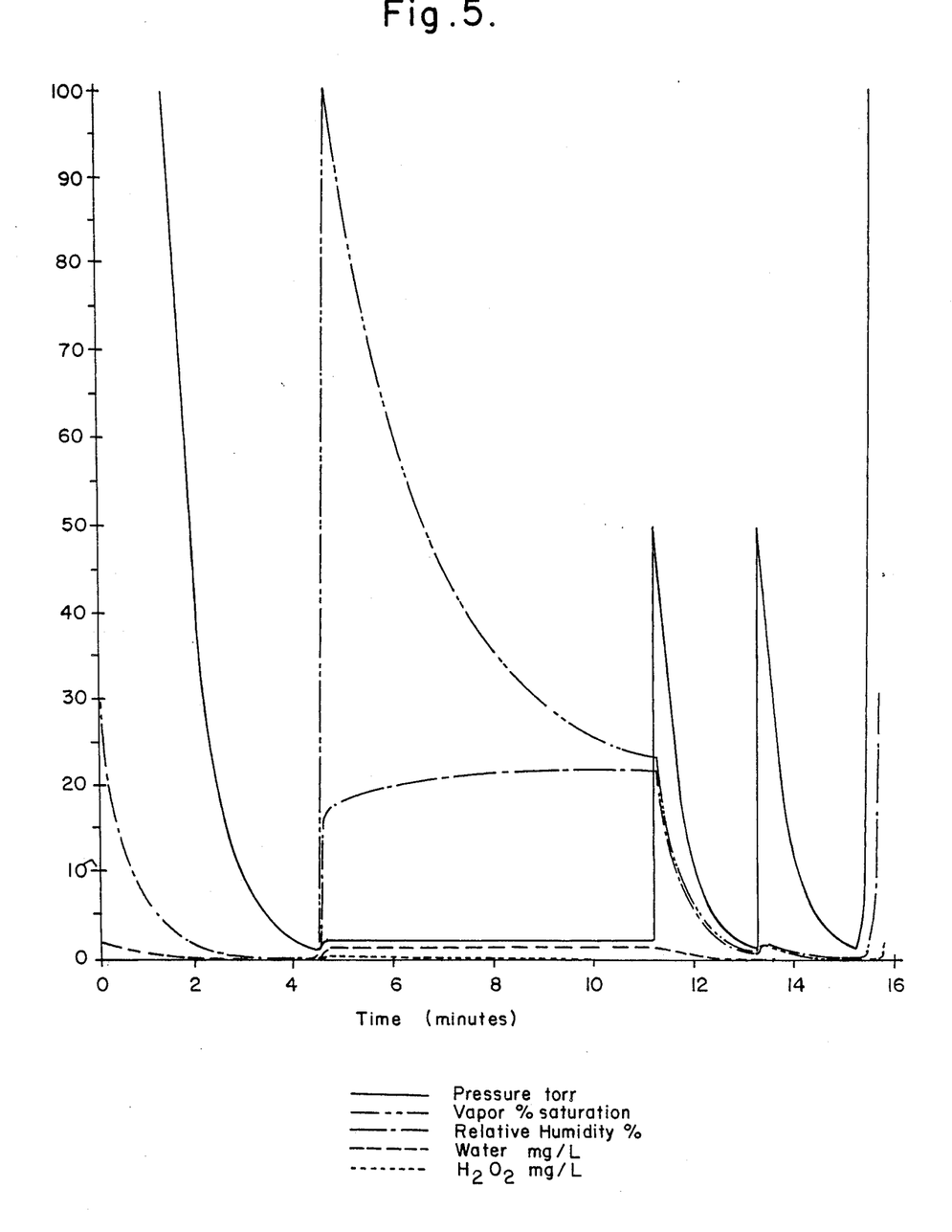
FIG. 5 is a graph showing the projected decrease in the degree of saturation of the vapor mixture in the simulation of a hydrogen peroxide sterilization cycle wherein a 30 wt% hydrogen peroxide and water vapor mixture is injected in a single injection into an evacuated sterilization chamber and held for a time with no make-up injections.
Figure 6:
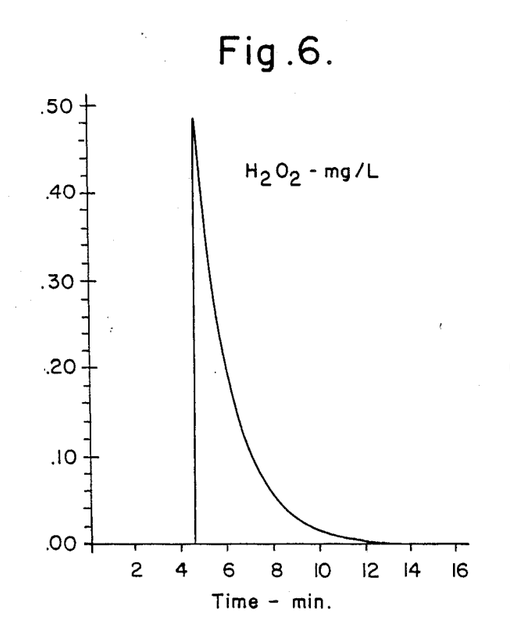
FIG. 6 is a graph showing the projected decrease in hydrogen peroxide concentration over time based on the sterilization cycle of FIG. 5.
Figure 7:
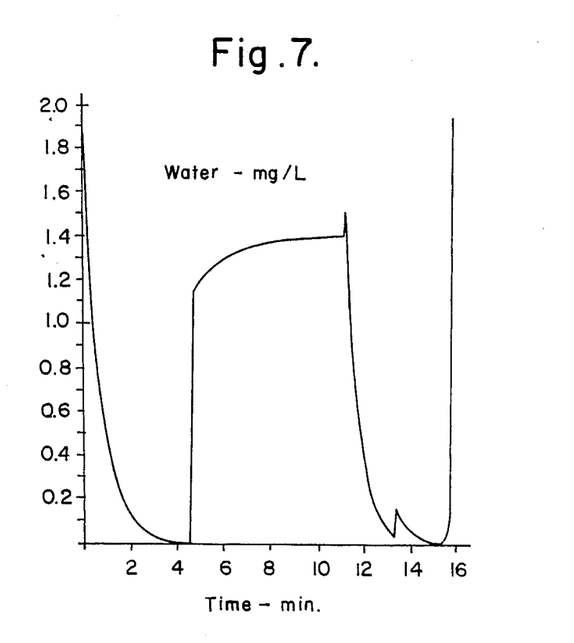
FIG. 7 is a graph showing the projected rise in water vapor concentration over time based on the sterilization cycle of FIG. 5.

To illustrate the problem of hydrogen peroxide degradation, refer to FIGS. 5 through 7, which simulate the activity within an evacuated 49.29 L sterilization chamber at 4° C. when there is a single injection of 30 wt% hydrogen peroxide-water vapor.

In FIG. 5, the scale of the vertical axis runs from zero to 100. For the solid line this means zero to 100 mm Hg (rorr) pressure. Thus, atmospheric pressure (760 torr) is off scale. As the cycle starts (time=0) air is withdrawn from the chamber and the pressure decreased from 760 torr to about 2 torr. At time=4.5 minutes, a mixture of hydrogen peroxide and water vapors is injected into the chamber causing a small rise in pressure. The pressure thereafter appears nearly constant (the "hold period"), until time=11.2 minutes, when air is allowed into the chamber ("air break"), causing an abrupt rise in pressure to 50 torr. The chamber is again evacuated, followed by air to 50 torr, evacuation, and air to atmospheric.

The dashed line in FIG. 5 illustrates the degree of saturation of the hydrogen peroxide and water vapor mixture in the chamber. It peaks to 100% upon injection of vapors (time=4 5), as planned. Immediately, however, it drops, as hydrogen peroxide vapors decompose.

FIG. 6 shows hydrogen peroxide vapor concentration during this cycle. The concentration drops nearly to zero during the hold period. This is undesireable because sterilization requires the maintenance of an effective level of hydrogen peroxide vapor throughout the entire sterilization hold period.

FIG. 7 shows that water vapor concentration rises during the sterilization hold period as hydrogen peroxide decomposition produces water vapor (and oxygen).

One might expect that a reasonable way to counteract the decrease in hydrogen peroxide vapor concentration during the sterilization hold period would be to inject more hydrogen peroxide to replace the amount lost.

Figure 8:
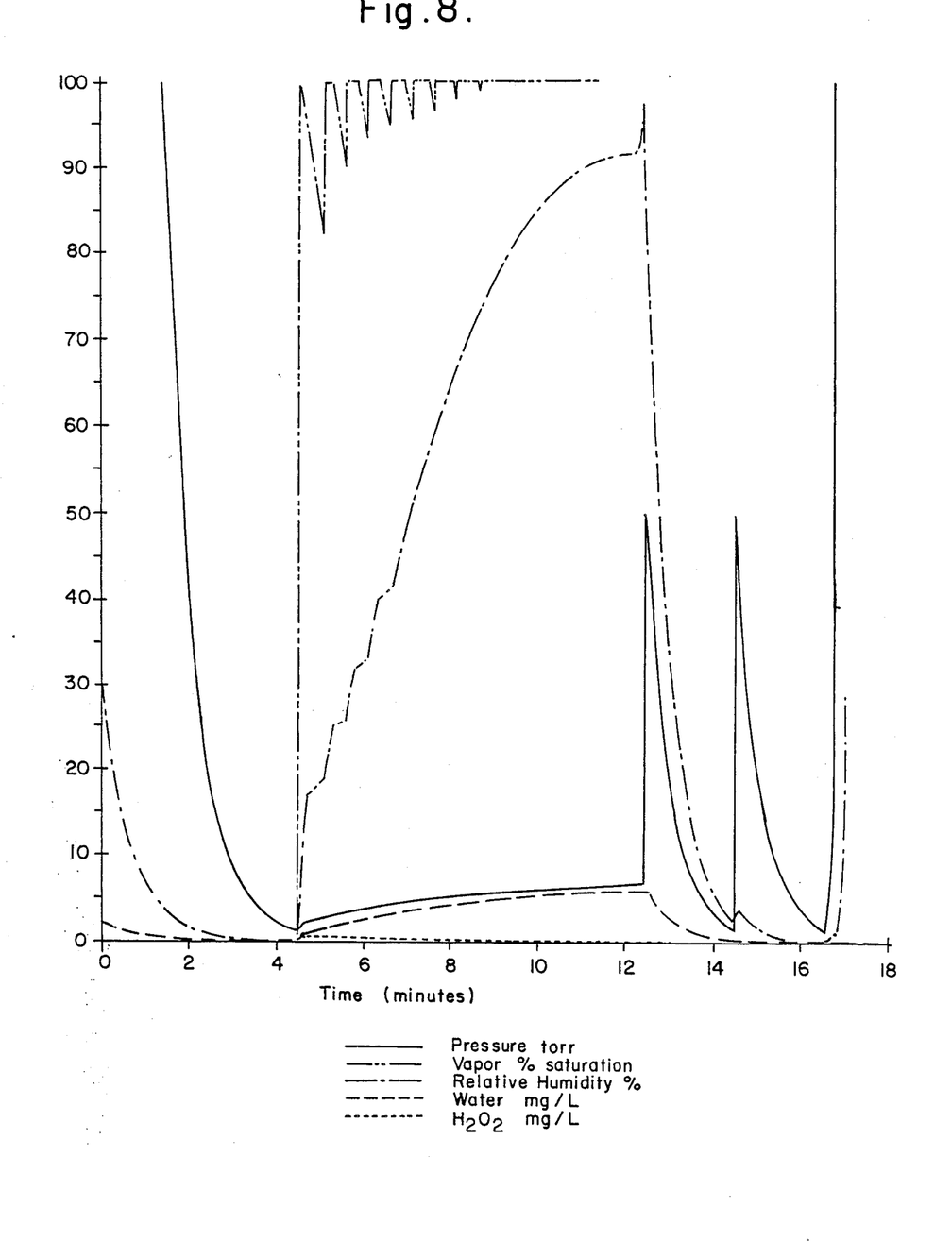
FIG. 8 is a graph showing the elevated degree of saturation of the vapor mixture in a sterilization cycle which incrementally compensates for lost hydrogen peroxide vapor by injecting a 30 wt% hydrogen peroxide and water vapor mixture in amounts equal to the amount of hydrogen peroxide vapor decomposed.

FIG. 8 illustrates a cycle which incrementally compensates for lost hydrogen peroxide vapor by injecting 30 wt% hydrogen peroxide-water vapor. The amount of hydrogen peroxide vapor injected equals the amount of hydrogen peroxide vapor decomposed since the last injection. The pressure trace reflects the small pressure rises with each increment. The vapor saturation trace shows that each injection reaches saturation.

Figure 9:
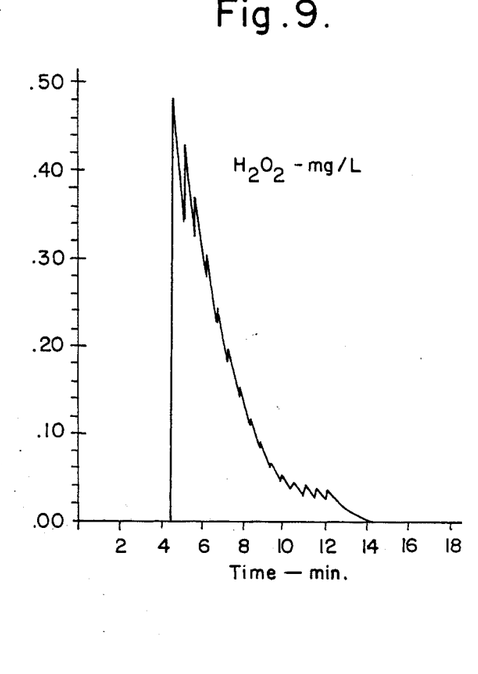
FIG. 9 is a graph showing the hydrogen peroxide vapor concentration over time based on the sterilization cycle of FIG. 8.
Figure 10:
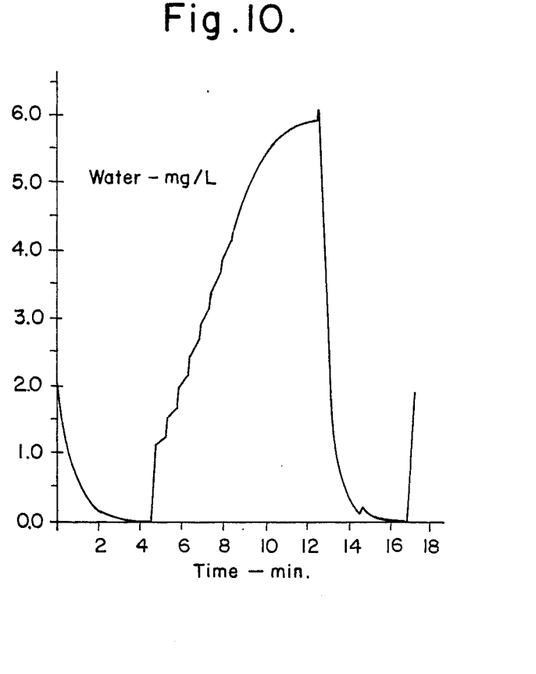
FIG. 10 is a graph showing the water vapor concentration over time based on the sterilization cycle of FIG. 8.
Figure 11:
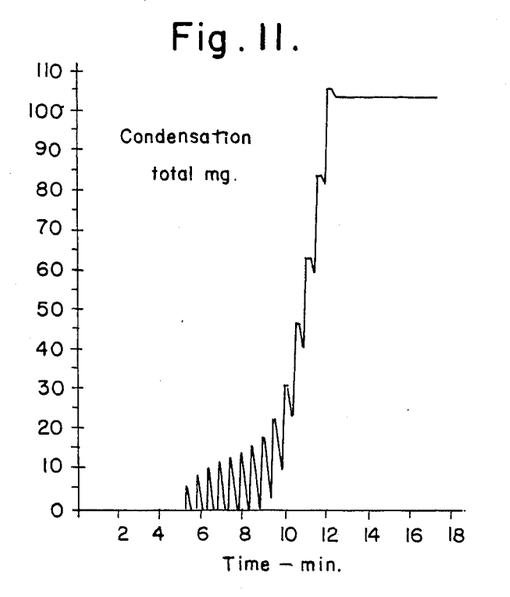
FIG. 11 is a graph showing the degree of condensation over time based on the sterilization cycle of FIG. 8.

FIG. 9 depicts the hydrogen peroxide vapor concentration associated with FIG. 8. Hydrogen peroxide vapor decreases almost as fast as it did without compensating injections. This is because water vapor concentration increases rapidly (See FIG. 10), due partly to decomposition of hydrogen peroxide vapor, but mostly from water vapor accompanying the hydrogen peroxide vapor in the compensating injections. As a result, the saturation limit decreases. The compensating injections exceed the saturation limit, causing condensation of hydrogen peroxide and some water. FIG. 11 shows the amount of condensate increasing from zero to 2.1 mg/L (105 mg condensate / 49.29 L chamber volume) because of the compensating injections.

The optimum hydrogen peroxide vapor sterilization method of the present invention overcomes the problems of hydrogen peroxide vapor degradation and condensation by employing knowledge concerning the changing saturation limit of hydrogen peroxide vapor during the sterilization cycle, particularly during the sterilization hold period, and introducing intermittent make-up injections of the hydrogen peroxide-water vapor mixture wherein the amount of each make-up injection maintains the hydrogen peroxide vapor concentration at a level necessary for effective sterilization but less than that which would raise the concentration of the vapor mixture to the saturation limit which will be present in the chamber immediately following such make-up injection at that point during the sterilization hold period.

Figure 1:
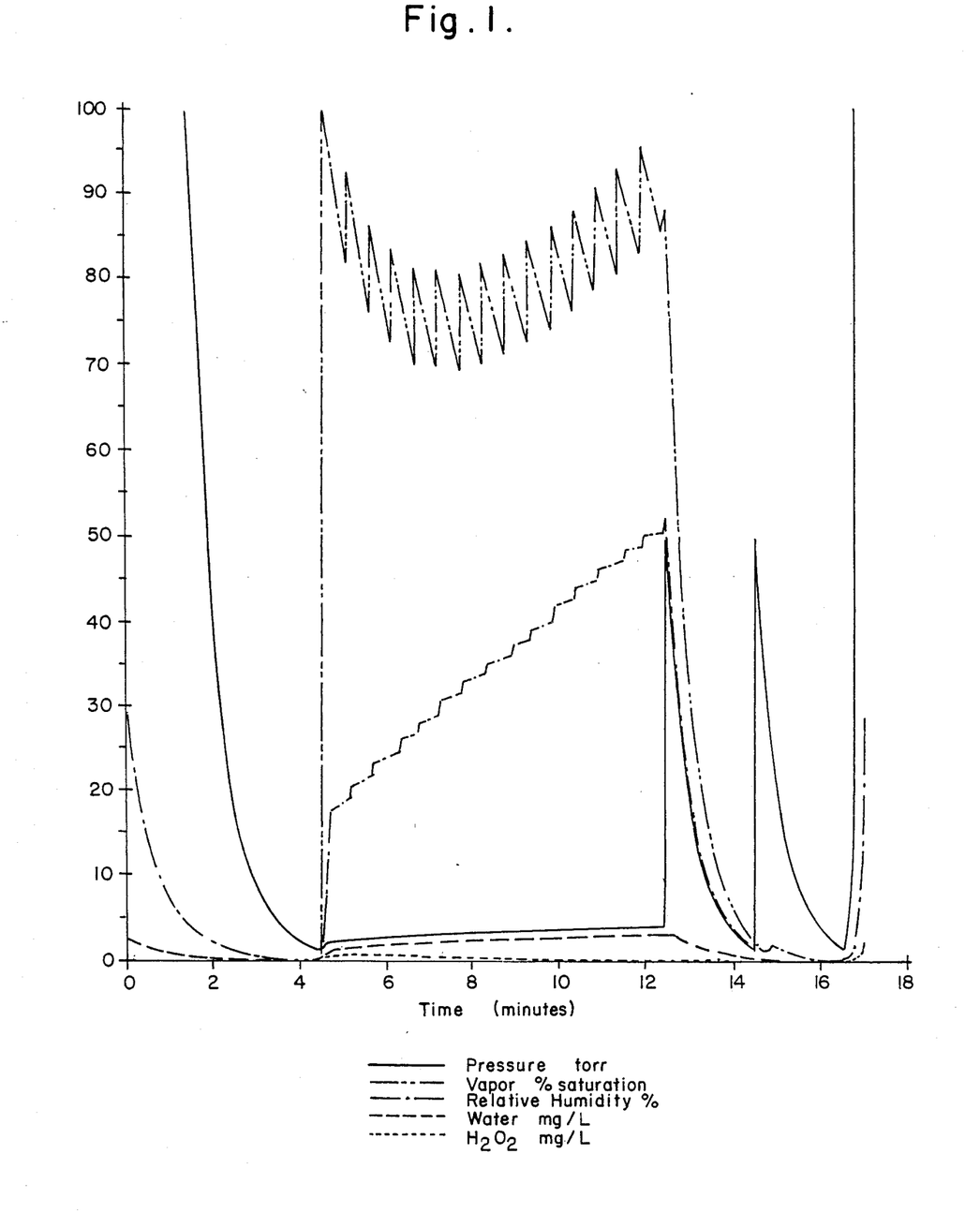
FIG. 1 is a graph showing a preferred embodiment of the optimum hydrogen peroxide vapor sterilization method of the present invention wherein a 30 wt% hydrogen peroxide and water vapor mixture is injected into an evacuated sterilization chamber and followed by a plurality of make-up injections.
Figure 2:
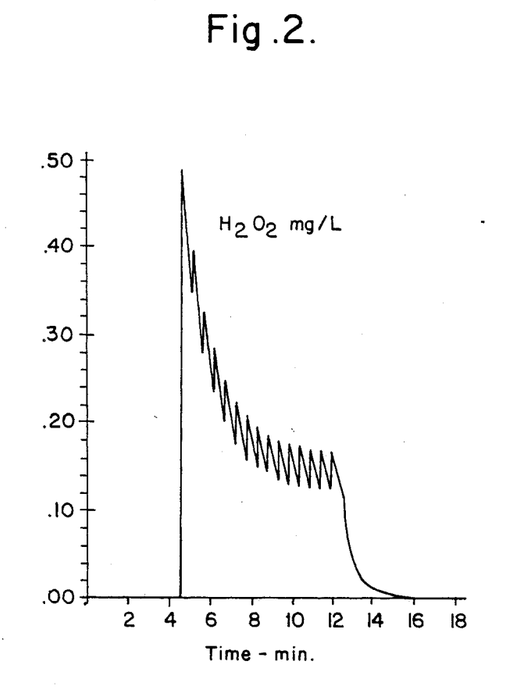
FIG. 2 is a graph showing the hydrogen peroxide vapor concentration over time based on the sterilization cycle of FIG. 1.
Figure 3:
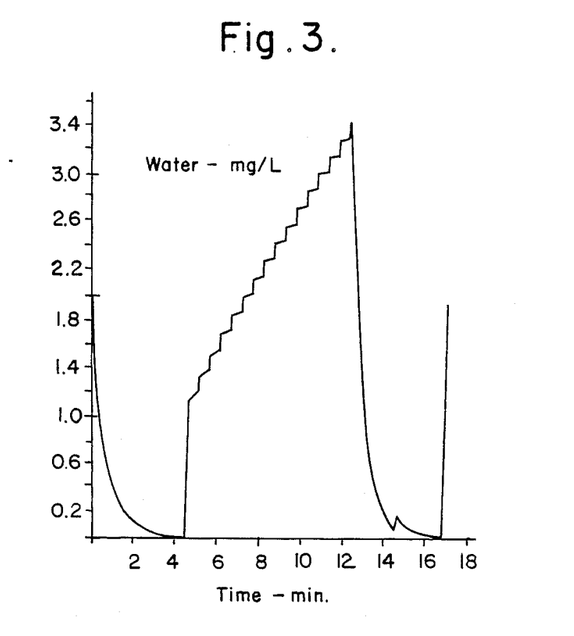
FIG. 3 is a graph showing the water vapor concentration over time based on the sterilization cycle of FIG. 1.

FIG. 1 illustrates the improved approach to the dilemma under the same conditions as those represented in FIGS. 5 and 8. As FIG. 2 illustrates, the hydrogen peroxide vapor concentration does not decrease as rapidly as it would in the other approaches represented in FIGS. 6 and 9. FIG. 3 illustrates the rise in water vapor concentration during the sterilization hold period of the sterilization cycle of the present invention.

The optimum hydrogen peroxide vapor sterilization method can be practiced in a vacuum chamber, as illustrated in the Figures, or in a static chamber. The method is not pressure dependent. In addition, the sterilization system would require a source of the desired hydrogen peroxide and water mixture, a vaporizer and valves capable of delivering precisely measured variable amounts of the hydrogen peroxide-water mixture to the vaporizer and then into the chamber. Because the timing and amounts of the vapor mixture to be delivered to the chamber are so important, a suitably programmed computer for controlling the injections is also desirable.

The purpose of the method is to maximize hydrogen peroxide vapor exposure during the cycle. Maximum exposure can result in reduced cycle time and/or greater assurance of sterilization. The sterilization cycle shown in FIG. 1 includes the steps of evacuating a sterilization chamber of a predetermined volume, injecting a hydrogen peroxide-water vapor mixture of a desired percent composition into the sterilization chamber at a desired temperature in an amount up to the amount necessary to reach the saturation limit of the vapor mixture associated with the volume cf the chamber, the temperature and the concentration of the vapor mixture, and injecting a plurality of intermittent make-up injections of the vapor mixture at a rate based on the rate of degradation of hydrogen peroxide vapor within the chamber. The amount of the vapor mixture in each such make-up injection is preferably just below the hydrogen peroxide concentration which would reach the saturation limit of the vapor mixture which will be present in the chamber immediately following each such make-up injection. The make-up injections are continued through the sterilization hold period of the cycle to maintain an optimum level of hydrogen peroxide vapor within the chamber necessary for effective sterilization without inducing appreciable condensation.

Following the sterilization hold period, the vapor mixture is exhausted from the chamber. The chamber is then aerated and again exhausted to ensure the complete removal of all of the sterilant vapor mixture. The aeration and evacuation steps may be repeated before the chamber is returned to atmospheric pressure.

FIGS. 1–3 were constructed based on the sterilization cycle data set forth in Table I below.

TABLE I $H_2O_2$ CYCLE IN 49.29 L CHAMBER AT 4° C.

| step | TIME min. | $H_2O_2$ mg/L | $H_2O_2$ satn mg/L | Water mg/L | RH % | VAPOR % satn | P torr | AMOUNT INJCTD |
|---|---|---|---|---|---|---|---|---|
| Close Door | 0.00 | 0.000 | | 1.94 | 30.00 | | 760.0 | 0.0 |
| vacuum/start | 0.45 | 0.000 | 0.00 | 1.00 | 15.45 | 15.5 | 391.5 | 0.0 |
| vacuum/mid | 2.25 | 0.000 | 0.00 | 0.07 | 1.09 | 1.1 | 27.6 | 0.0 |
| vacuum/end | 4.50 | 0.000 | 0.00 | 0.00 | 0.04 | 0.0 | 1.0 | 0.0 |
| inject/start | 4.50 | 0.049 | 0.48 | 0.12 | 1.80 | 10.1 | 1.1 | 8.0 |
| inject/mid | 4.60 | 0.243 | 0.49 | 0.57 | 8.84 | 50.1 | 1.7 | 40.0 |
| inject/end | 4.70 | 0.486 | 0.49 | 1.14 | 17.64 | 100.0 | 2.3 | 80.0 |
| hold/start | 4.78 | 0.459 | 0.47 | 1.15 | 17.86 | 96.6 | 2.3 | 80.0 |
| hold/end | 5.20 | 0.344 | 0.42 | 1.21 | 18.81 | 81.8 | 2.3 | 80.0 |
| inject | 5.20 | 0.392 | 0.43 | 1.33 | 20.57 | 91.8 | 2.5 | 88.0 |
| hold/start | 5.30 | 0.370 | 0.42 | 1.34 | 20.75 | 88.9 | 2.5 | 88.0 |
| hold/end | 5.70 | 0.277 | 0.36 | 1.39 | 21.51 | 76.2 | 2.5 | 88.0 |
| inject | 5.70 | 0.326 | 0.38 | 1.50 | 23.27 | 86.4 | 2.6 | 96.0 |
| hold/start | 5.80 | 0.308 | 0.37 | 1.51 | 23.42 | 83.8 | 2.6 | 96.0 |
| hold/end | 6.22 | 0.231 | 0.32 | 1.55 | 24.05 | 72.5 | 2.6 | 96.0 |
| inject | 6.22 | 0.279 | 0.34 | 1.67 | 25.81 | 82.9 | 2.7 | 104.0 |
| hold/start | 6.32 | 0.264 | 0.33 | 1.67 | 25.94 | 80.6 | 2.7 | 104.0 |
| hold/end | 6.74 | 0.197 | 0.28 | 1.71 | 26.49 | 70.4 | 2.7 | 104.0 |
| inject | 6.74 | 0.246 | 0.30 | 1.82 | 28.25 | 81.1 | 2.9 | 112.0 |
| hold/start | 6.84 | 0.232 | 0.29 | 1.83 | 28.36 | 78.9 | 2.9 | 112.0 |
| hold/end | 7.26 | 0.174 | 0.25 | 1.86 | 28.84 | 69.4 | 2.9 | 112.0 |
| inject | 7.26 | 0.223 | 0.28 | 1.97 | 30.60 | 80.4 | 3.0 | 120.0 |
| hold/start | 7.36 | 0.210 | 0.27 | 1.98 | 30.70 | 78.3 | 3.0 | 120.0 |
| hold/end | 7.78 | 0.157 | 0.23 | 2.01 | 31.13 | 69.4 | 3.0 | 120.0 |
| inject | 7.78 | 0.206 | 0.26 | 2.12 | 32.89 | 80.6 | 3.1 | 128.0 |
| hold/start | 7.88 | 0.195 | 0.25 | 2.13 | 32.99 | 78.6 | 3.1 | 128.0 |
| hold/end | 8.30 | 0.146 | 0.21 | 2.15 | 33.39 | 70.0 | 3.1 | 128.0 |
| inject | 8.30 | 0.194 | 0.24 | 2.27 | 35.15 | 81.4 | 3.3 | 136.0 |
| hold/start | 8.40 | 0.184 | 0.23 | 2.27 | 35.24 | 79.5 | 3.3 | 136.0 |
| hold/end | 8.82 | 0.138 | 0.19 | 2.30 | 35.62 | 71.1 | 3.3 | 136.0 |
| inject | 8.82 | 0.186 | 0.23 | 2.41 | 37.38 | 82.7 | 3.4 | 144.0 |
| hold/start | 8.92 | 0.176 | 0.22 | 2.42 | 37.46 | 80.9 | 3.4 | 144.0 |
| hold/end | 9.34 | 0.132 | 0.18 | 2.44 | 37.82 | 72.6 | 3.4 | 144.0 |
| inject | 9.34 | 0.180 | 0.21 | 2.55 | 39.58 | 84.4 | 3.5 | 152.0 |
| hold/start | 9.44 | 0.170 | 0.21 | 2.56 | 39.67 | 82.5 | 3.5 | 152.0 |
| hold/end | 9.86 | 0.128 | 0.17 | 2.58 | 40.02 | 74.3 | 3.5 | 152.0 |
| inject | 9.86 | 0.176 | 0.20 | 2.70 | 41.78 | 86.3 | 3.7 | 160.0 |
| hold/start | 9.96 | 0.166 | 0.20 | 2.70 | 41.86 | 84.5 | 3.7 | 160.0 |
| hold/end | 10.38 | 0.125 | 0.16 | 2.72 | 42.20 | 76.2 | 3.7 | 160.0 |
| inject | 10.38 | 0.173 | 0.20 | 2.84 | 43.96 | 88.4 | 3.8 | 168.0 |
| hold/start | 10.48 | 0.164 | 0.19 | 2.84 | 44.04 | 86.6 | 3.8 | 168.0 |
| hold/end | 10.90 | 0.123 | 0.16 | 2.86 | 44.38 | 78.3 | 3.8 | 168.0 |
| inject | 10.90 | 0.171 | 0.19 | 2.98 | 46.14 | 90.7 | 3.9 | 176.0 |
| hold/start | 11.00 | 0.162 | 0.18 | 2.98 | 46.22 | 88.8 | 3.9 | 176.0 |
| hold/end | 11.42 | 0.121 | 0.15 | 3.00 | 46.55 | 80.5 | 3.9 | 176.0 |
| inject | 11.42 | 0.170 | 0.18 | 3.12 | 48.31 | 93.0 | 4.1 | 184.0 |
| hold/start | 11.52 | 0.160 | 0.18 | 3.12 | 48.39 | 91.1 | 4.1 | 184.0 |
| hold/end | 11.94 | 0.120 | 0.14 | 3.14 | 48.72 | 82.8 | 4.1 | 184.0 |
| inject | 11.94 | 0.169 | 0.18 | 3.26 | 50.48 | 95.4 | 4.2 | 192.0 |
| hold/start | 12.04 | 0.159 | 0.17 | 3.26 | 50.56 | 93.5 | 4.2 | 192.0 |
| hold/end | 12.46 | 0.119 | 0.14 | 3.28 | 50.89 | 85.1 | 4.2 | 192.0 |
| airbreak | 12.51 | 0.119 | 0.14 | 3.40 | 52.69 | 87.1 | 50.0 | 192.0 |
| vac | 14.51 | 0.002 | 0.14 | 0.07 | 1.05 | 1.7 | 1.0 | 192.0 |
| airbreak | 14.56 | 0.002 | 0.06 | 0.19 | 2.99 | 3.8 | 50.0 | 192.0 |
| vac | 16.56 | 0.000 | 0.06 | 0.00 | 0.06 | 0.1 | 1.0 | 192.0 |
| airbreak | 17.06 | 0.000 | 0.00 | 1.94 | 30.02 | 28.9 | 760.0 | 192.0 |

The amount of vapor mixture which should be injected in each make up injection can be determined either by continuously monitoring, directly or indirectly, the hydrogen peroxide vapor concentration and the relative humidity within the chamber, or by predicting the concentration of hydrogen peroxide and water vapors over time and relative humidity.

In either situation, whether the amount injected is measured or predetermined, the amount must be at most, just below the amount that would saturate the vapor mixture and cause condensation. Because the concentration of the incoming hydrogen peroxide vapor is known, the hydrogen peroxide vapor concentration following the injection can be monitored indirectly by calculations based on continuously measuring the pressure, temperature and time into the sterilization hold period. A direct method of monitoring hydrogen peroxide vapor concentration is disclosed in the Cummings U.S. Pat. No. 4,843,867 entitled "System for Monitoring Sterilant Vapor Concentration" filed simultaneously herewith and incorporated herein by reference. Any other suitable direct method of monitoring hydrogen peroxide vapor concentration can be used.

The saturation limit of the vapors will vary depending on the percent composition of the hydrogen peroxide and warer vapor mixture, the temperature and the chamber volume. For purposes of discussing rhe preferred embodiment, the chamber volume is assumed to be 49.29 liters, the injected vapor mixture is a 30 wt% hydrogen peroxide and water mixture and the temperature is 4° C. The graphs in FIGS. 1 through 11 are constructed on the basis of those parameters. Other percent compositions, temperatures and chamber volumes can be used with appropriate modification in the calculations.

Figure 4:
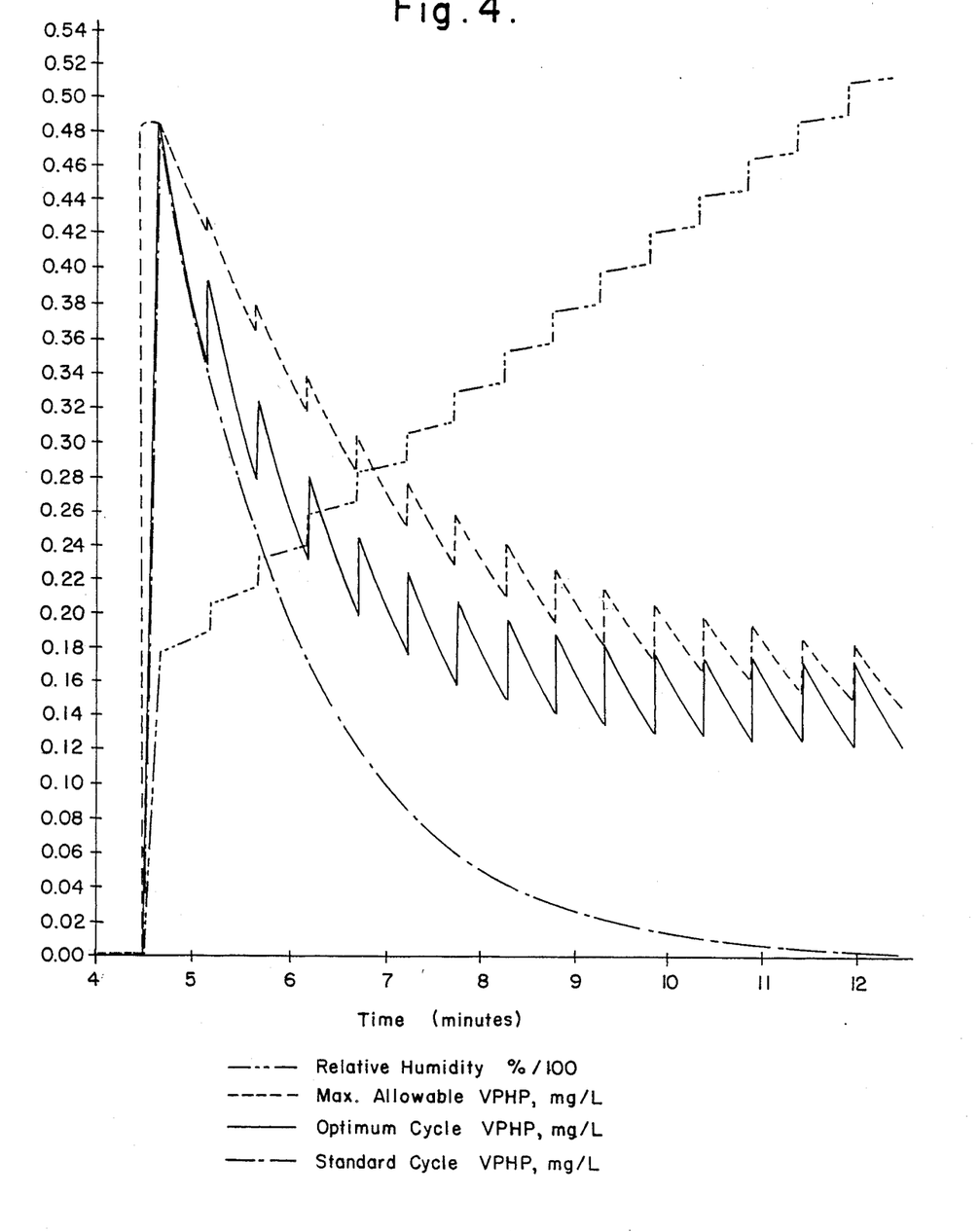
FIG. 4 is a graph comparing relative humidity, maximum allowable hydrogen peroxide vapor concentration, the standard hydrogen peroxide vapor concentration over time obtained from a single injection of vapor and the optimum hydrogen peroxide vapor concentration over time based on the preferred embodiment of the sterilization method of the present invention.

The graph in FIG. 4 illustrates how the optimum sterilization cycle can keep the level of hydrogen peroxide vapor in the chamber far above the standard hydrogen peroxide vapor level observed with a single injection and no make-up injections, but slightly below the maximum allowable level to avoid reaching the saturation limit of the vapor mixture. The maximum allowable level decreases with increasing humidity in accordance with the tabulations in Table I. Table II is provided to help illustrate this fact, as set forth below.

process and should be avoided or kept to a minimum for best results. In addition, for catalytic surfaces, the greater the surface to volume ratio, the faster the rate of the degradation reaction will be. It is noted that for every gram of hydrogen peroxide which degrades to water and oxygen, 0.53 g water and 0.47 g oxygen are produced. At 4° C. 100% relative humidity corresponds to 6.4 mg water vapor per Liter.

The times in FIG. 4 coordinate with times in Table I and FIGS. 1 through 11. Thus, time 4.5 represents the point at which the hydrogen peroxide-water vapor mixture is initially injected into the sterilization chamber. About half a minute later (time =5.2), a make-up injection of about 0.16 mg/L 30 wt% hydrogen peroxide-water vapor is introduced into the chamber, raising the hydrogen peroxide concentration by about 0.05 mg/L to about .39 mg/L (See Table I). Additional make-up injections are made about every thirty seconds. With each make-up injection and the continuing degradation of the hydrogen peroxide, the relative humidity increases and the maximum allowable hydrogen peroxide level within the chamber decreases, as shown. Momentary increases in the maximum allowable vapor phase hydrogen peroxide level occur with each make-up injection because the incoming 30 wt% mixture enriches the hydrogen peroxide-water vapor ratio. The optimum hydrogen peroxide concentration is maintained by carefully calculated make-up injections. For comparison, the hydrogen peroxide concentration which would be in the chamber if there were no make-up injections is also presented by a curve ("Standard Cycle") on the graph in FIG. 4.

The curve of FIG. 4 representing the maximum al-

TABLE II

MAXIMUM HYDROGEN PEROXIDE VAPOR CONCENTRATIONS (mg/liter) FROM 30% BY WEIGHT LIQUID SOLUTION FLASH VAPORIZED AND MAINTAINED AT VARIOUS TEMPERATURES AND RELATIVE HUMIDITIES

| VAPOR TEMPERATURE (°C.) | MAX. $H_2O_2$ VAPOR CONCENTRATION (mg/liter) RELATIVE HUMIDITY | | | |
|---|---|---|---|---|
| | 0% | 20% | 40% | 80% |
| 1 | 0.389 | 0.263 | 0.168 | 0.041 |
| 2 | 0.419 | 0.284 | 0.180 | 0.046 |
| 3 | 0.452 | 0.307 | 0.197 | 0.049 |
| 4 | 0.487 | 0.332 | 0.208 | 0.052 |
| 5 | 0.524 | 0.357 | 0.228 | 0.058 |
| 6 | 0.563 | 0.385 | 0.245 | 0.061 |
| 7 | 0.606 | 0.415 | 0.264 | 0.066 |
| 8 | 0.651 | 0.444 | 0.287 | 0.073 |
| 9 | 0.699 | 0.478 | 0.303 | 0.078 |
| 10 | 0.750 | 0.513 | 0.325 | 0.081 |
| 20 | 1.48 | 1.02 | 0.661 | 0.166 |
| 30 | 2.79 | 1.94 | 1.26 | 0.302 |
| 40 | 5.03 | 3.54 | 2.28 | 0.519 |
| 60 | 14.6 | 10.4 | 6.8 | 1.4 |
| 80 | 37.4 | 26.8 | 17.5 | 3.3 |

The graph of FIG. 4 is based on there being a half life of one minute for hydrogen peroxide degradation. The actual rate of hydrogen peroxide degradation is affected by the type of materials within the chamber and the chamber itself. Some materials catalyze the degradation lowable hydrogen peroxide vapor concentration which corresponds to varying relative humidities, vapor phase hydrogen peroxide/water vapor ratio and temperatures was calculated using data obtained from Tables III and IV set forth below.

TABLE III

| | TOTAL VAPOR PRESSURE (mm · Hg) OF HYDROGEN PEROXIDE-WATER SOLUTION* | | | | | | | | | | |
|---|---|---|---|---|---|---|---|---|---|---|---|
| Temp. | Mole Fraction Hydrogen Peroxide in Liquid | | | | | | | | | | |
| (°C.) | 0 | 0.1 | 0.2 | 0.3 | 0.4 | 0.5 | 0.6 | 0.7 | 0.8 | 0.9 | 1.0 |
| 0 | 4.58 | 4.06 | 3.45 | 2.81 | 2.20 | 1.66 | 1.21 | 0.856 | 0.593 | 0.404 | 0.272 |
| 10 | 9.20 | 8.17 | 6.96 | 5.70 | 4.49 | 3.42 | 2.53 | 1.83 | 1.30 | 0.915 | 0.642 |
| 20 | 17.5 | 15.6 | 13.3 | 10.9 | 8.69 | 6.68 | 5.00 | 3.66 | 2.64 | 1.89 | 1.36 |

TABLE III-continued
TOTAL VAPOR PRESSURE (mm · Hg) OF HYDROGEN PEROXIDE-WATER SOLUTION*

| Temp. (°C.) | Mole Fraction Hydrogen Peroxide in Liquid | | | | | | | | | | |
|---|---|---|---|---|---|---|---|---|---|---|---|
| | 0 | 0.1 | 0.2 | 0.3 | 0.4 | 0.5 | 0.6 | 0.7 | 0.8 | 0.9 | 1.0 |
| 25 | 23.7 | 21.1 | 18.1 | 14.9 | 11.9 | 9.17 | 6.90 | 5.09 | 3.71 | 2.69 | 1.95 |
| 30 | 31.8 | 28.3 | 24.3 | 20.1 | 16.0 | 12.4 | 9.41 | 6.99 | 5.14 | 3.77 | 2.77 |
| 40 | 55.3 | 49.3 | 42.4 | 35.2 | 28.3 | 22.2 | 17.0 | 12.8 | 9.55 | 7.14 | 5.36 |
| 50 | 92.6 | 82.5 | 71.1 | 59.3 | 48.1 | 37.9 | 29.3 | 22.4 | 17.0 | 12.9 | 9.90 |
| 60 | 149 | 133 | 115 | 96.6 | 78.7 | 62.6 | 49.0 | 37.8 | 29.1 | 22.5 | 17.5 |
| 70 | 234 | 209 | 181 | 152 | 125 | 100 | 79.0 | 61.8 | 48.2 | 37.8 | 20.8 |
| 80 | 355 | 318 | 216 | 233 | 192 | 155 | 124 | 97.8 | 77.2 | 61.3 | 49.1 |
| 90 | 526 | 471 | 410 | 348 | 289 | 235 | 189 | 150 | 120 | 96.5 | 78.2 |
| 100 | 760 | 682 | 595 | 507 | 422 | 346 | 280 | 226 | 182 | 148 | 121 |
| 110 | 1074 | 965 | 845 | 722 | 605 | 499 | 407 | 331 | 269 | 221 | 182 |
| 120 | 1489 | 1339 | 1175 | 1008 | 848 | 704 | 578 | 474 | 389 | 322 | 269 |
| 130 | 2025 | 1824 | 1604 | 1381 | 1168 | 974 | 807 | 666 | 552 | 460 | 387 |
| 140 | 2709 | 2443 | 2153 | 1860 | 1580 | 1326 | 1105 | 919 | 767 | 645 | 546 |
| 150 | 3568 | 3222 | 2847 | 2467 | 2105 | 1776 | 1489 | 1247 | 1048 | 887 | 755 |

*reprinted from W. C. Schumb, et al. "Hydrogen Peroxide", pp. 221-227 (Reinhold pub. 1955) based on experimental data from several sources.

TABLE IV
VAPOR COMPOSITION (MOLE FRACTION H2O2) OVER HYDROGEN PEROXIDE-WATER SOLUTIONS*

| Temp. (°C.) | Mole Fraction Hydrogen Peroxide in Liquid | | | | | | | | |
|---|---|---|---|---|---|---|---|---|---|
| | 0.1 | 0.2 | 0.3 | 0.4 | 0.5 | 0.6 | 0.7 | 0.8 | 0.9 |
| 0 | 0.002 | 0.006 | 0.015 | 0.031 | 0.060 | 0.112 | 0.202 | 0.352 | 0.600 |
| 10 | 0.003 | 0.008 | 0.018 | 0.037 | 0.070 | 0.128 | 0.224 | 0.381 | 0.626 |
| 20 | 0.003 | 0.009 | 0.020 | 0.041 | 0.077 | 0.138 | 0.238 | 0.397 | 0.640 |
| 25 | 0.003 | 0.010 | 0.022 | 0.044 | 0.081 | 0.144 | 0.247 | 0.407 | 0.648 |
| 30 | 0.003 | 0.010 | 0.023 | 0.046 | 0.085 | 0.151 | 0.255 | 0.417 | 0.656 |
| 40 | 0.004 | 0.012 | 0.026 | 0.052 | 0.094 | 0.163 | 0.272 | 0.435 | 0.671 |
| 50 | 0.005 | 0.014 | 0.030 | 0.057 | 0.103 | 0.175 | 0.287 | 0.452 | 0.684 |
| 60 | 0.005 | 0.015 | 0.033 | 0.063 | 0.111 | 0.187 | 0.302 | 0.468 | 0.696 |
| 70 | 0.006 | 0.017 | 0.036 | 0.068 | 0.120 | 0.199 | 0.316 | 0.482 | 0.707 |
| 80 | 0.007 | 0.019 | 0.040 | 0.074 | 0.128 | 0.210 | 0.329 | 0.495 | 0.716 |
| 90 | 0.007 | 0.021 | 0.043 | 0.080 | 0.136 | 0.221 | 0.342 | 0.508 | 0.725 |
| 100 | 0.008 | 0.023 | 0.047 | 0.085 | 0.144 | 0.231 | 0.354 | 0.519 | 0.733 |
| 110 | 0.009 | 0.025 | 0.051 | 0.091 | 0.152 | 0.241 | 0.365 | 0.530 | 0.740 |
| 120 | 0.010 | 0.027 | 0.054 | 0.097 | 0.160 | 0.251 | 0.376 | 0.540 | 0.747 |
| 130 | 0.011 | 0.029 | 0.058 | 0.102 | 0.168 | 0.260 | 0.386 | 0.549 | 0.753 |
| 140 | 0.012 | 0.031 | 0.061 | 0.108 | 0.175 | 0.269 | 0.396 | 0.558 | 0.758 |
| 150 | 0.013 | 0.033 | 0.065 | 0.113 | 0.182 | 0.278 | 0.403 | 0.566 | 0.763 |

*reprinted from W. C. Schumb, et al. "Hydrogen Peroxide", pp. 221-227 (Reinhold pub. 1955) based on experimental data from several sources.

In order to predetermine the optimum hydrogen peroxide vapor concentration for a particular sterilization cycle, a series of complex and interactive calculations must be made. First, the saturation limit of the vapor mixture must be determined. Although the calculations are based on known data it would not be immediately apparent to use the data as described herein because the data of Tables III and IV describe natural conditions wherein the vapors are in equilibrium with the corresponding mixtures. The vapor mixture of the present method is a binary mixture which is preferably flash vaporized according to the method described in Bier U.S. Pat. No. 4,642,165 the relevant portions of which are hereby incorporated herein by reference. The forced vaporization produces higher concentrations of hydrogen peroxide in the vapor mixture than would be found with natural vaporization from a solution.

In a closed system, a liquid mixture containing $X_h$ mole fraction hydrogen peroxide and $X_w$ mole fraction water is in equilibrium with a saturated vapor mixture of $Y_h$ mole fraction hydrogen peroxide and $Y_w$ mole fraction water whose concentrations are proportional to partial pressures $P_h$ and $P_w$, respectively. The partial pressures, $P_h$ and $P_w$ equal the total pressure, P. ($P_h + P_w = P$). The vapor composition $Y_h$ and $Y_w$ equals one ($Y_h + Y_w = 1$) and the liquid composition, $X_h$ and $X_w$ also equals one ($X_h + X_w = 1$). The partial pressure equals the product of the total pressure and the vapor composition ($P_h = Y_h*P$; $P_w = Y_w*P$).

The saturation limit can be determined by measuring vapor concentrations in equilibrium with liquid mixtures. The data in Tables III and IV represents known vapor pressure and vapor composition over liquid mixtures of hydrogen peroxide and water based on measurements of such mixtures gathered from several sources. Vapor concentrations at saturation can be determined for a given temperature by combining vapor composition data from Table IV with vapor pressure data from Table III.

For example, Table IV shows that at 20° C, vapor composed of 0.020 mole fraction hydrogen peroxide ($Y_h = 0.020$, $Y_w = 0.980$) would be in equilibrium with liquid composed of 0.3 mole fraction hydrogen peroxide ($X_h = 0.3$, $X_w = 0.7$). Table III provides that, ar 20° C., total vapor pressure ($P_h + P_w$) over 0.3 mole fraction hydrogen peroxide mixture is 10.9 mm Hg. The ideal gas law, ($PV = nRT$) together with the respective molecular weights of the vapors, can be used to calculate the concentrations of the hydrogen peroxide and water vapor components of the vapor mixture according to the following relationships.

$$C = w/V = Mn/V = MYP/(RT)$$

where
C = the concentration of vapor, eg., mg/L
w = mass
V = Volume
M = molecular weight
n = moles of vapor
P = total vapor pressure
Y = vapor mole fraction
R = universal gas constant
T = temperature of vapor (and liquid)

In the present example, at 20° C. the saturated hydrogen peroxide vapor concentration is determined by the relationship $C = MYP/RT$, or $$\frac{(34.02 \text{ g/mole}) (0.02) (10.9 \text{ mm Hg})}{(760 \text{ mm Hg/atm}) \left(0.082 \frac{\text{liter-atm}}{\text{mole} - °K.}\right)(293° K.)} =$$

0.00041 g/L

The saturated water vapor concentration is similarly determined.

$$\frac{(18.02 \text{ g/mole})(0.98)(10.9 \text{ mm Hg})}{(760 \text{ mm Hg/atm})\left(0.082 \frac{\text{liter-atm}}{\text{mole} - {}^\circ \text{K.}}\right)(293^\circ \text{ K.})} = 0.0105 \text{ g/L}$$

Thus, at 20° C., in the presence of 10.5 mg/L water vapor, the saturation limit for hydrogen peroxide vapor is 0.41 mg/L. This process can be repeated for any combination of temperature and vapor composition by appropriate interpolation between values in Tables III and IV. For example, at 4° C. (the temperature of the sterilization method represented in the Figures) interpolating from the data in Tables III and IV and using the relationship C=MYP/RT, in the presence of 1.1 mg/L water vapor, the saturation limit for hydrogen peroxide vapor is about .5 mg/L, or a 30 wt% (0.185 mole fraction) hydrogen peroxide-water vapor mixture.

Alternatively, the equations, by which the data of the Tables were calculated, can be used. The equations given by W. C. Schumb, et al. supra at pp. 225-227, are set forth below:

$$P = Pw_o * Xw * \gamma w + Ph_o * (1 - Xw) * \gamma h$$

$$Yh = \frac{Ph_o * Xh * \gamma h}{P} = \frac{Ph_o * Xh \, \gamma h}{(Pw_o * Xw * \gamma w) + (Ph_o * Xh * \gamma h)}$$

wherein
P=total vapor pressure
$Pw_o$=vapor pressure of pure water
$Ph_o$=vapor pressure of anhydrous hydrogen peroxide
Xw=liquid mole fraction composition of water
Xh=liquid mole fraction composition of hydrogen peroxide
$\gamma w$=activity coefficient for water
$\gamma h$=activity coefficient for hydrogen peroxide
Yh=vapor mole fraction composition of hydrogen peroxide
*=multiplication symbol Formulas are also given by Schumb et al. supra. for the calculation of $Pw_o$ and $Ph_o$ as functions of temperature, and for the calculation of $\gamma w$ and $\gamma h$ as functions of temperature and liquid composition.

In practice, the water vapor concentration, and therefore, the corresponding saturation limit for hydrogen peroxide vapor in the sterilization cycle is not static, but constantly changing due to the degradation of the hydrogen peroxide vapor to water and oxygen. The calculations must be repeated for the changing conditions throughout the sterilization stage of the cycle. The calculation process is complex and iterative, when starting from vapor composition, and is best accomplished with the aid of a suitably programmed computer.

The method of the present invention requires knowledge of the amount of vapor of one composition that can be added to vapor of another composition and not exceed the new saturation limit which will result from the additional amount of vapor. The complexity of the situation can be realized if one visualizes incremental addition of the first composition (vapor A, the vapor mixture comprising make-up injection) to the second (vapor B, the vapor mixture within the chamber prior to a particular make-up injection). Each composition has an associated saturation limit. Addition of some of vapor A to vapor B changes the composition of vapor B and a new saturation limit applies. Another increment of vapor A added to vapor B further alters the composition of vapor B and the associated saturation limit.

The calculation of the amount of vapor A that can be added to vapor B to reach, but not exceed, the saturation limit was accomplished by an incremental approach. Compositions of vapor B and saturation limits resulting from incremental additions of vapor A were calculated. If the saturation limit was greater than the concentration in the new vapor B, another increment was calculated. If the saturation limit was exceeded, the calculation was backed up one step, and a smaller incremental addition was calculated. Eventually, the saturation limit on addition of vapor A was determined to the desired precision (0.2%).

Table II shows the results of those calculations for a few specific cases. Vapor A was 30 wt% (0.185 mole fraction) hydrogen peroxide and water vapor mixture (Yh=0.185, Yw=0.815. Vapor B initially contained only water vapor, no hydrogen peroxide. Water vapor concentrations head the columns of Table II, and are given as relative humidities (0%, 20%, 40%, 80%). The 0% column is for no water vapor, that is, vapor B is vacant initially. Thus, the 0% column shows the saturation limit of 30 wt% hydrogen peroxide/water vapor. For the other columns, the initial water vapor concentration varies with temperature.

To calculate the data of Table II, refer again to Table IV to find by interpolation the mole fraction liquid hydrogen peroxide corresponding to 0.185 mole fraction hydrogen peroxide vapor. Then refer to Table III to find the total vapor pressure corresponding to that mole fraction liquid hydrogen peroxide and temperature.

The total pressure obtained from Table III is used to calculate the saturated hydrogen peroxide and water vapor concentrations in mg/L according to the relationship C=MYP/RT as described previously.

For example, and ignoring for the moment the desired temperature conditions, from Table IV, a 0.185 mole fraction hydrogen peroxide vapor corresponds most nearly to 0.6 mole fraction liquid hydrogen peroxide at 60° C, which in turn from Table III, corresponds to 49.0 mm Hg total pressure of the hydrogen peroxide-water mixture.

Using the relationship C=MYP/RT, the concentrations of saturated hydrogen peroxide and water vapors at 0% relative humidity are 14.9 mg/L and 34.7 mg/L, respectively. Table II shows 14.6 mg/L as the saturation limit, rather than 14.9, because of minor differences between the processes of interpolation (used in this example) and iteration on the equations (used to construct Table II).

At 20% relative humidity, there is another source of water vapor in the chamber. When a 30 wt% hydrogen peroxide-water vapor mixture is injected, the new composition will have an actual hydrogen peroxide percentage composition at something less than 30 wt%. The concentration of hydrogen peroxide vapor at the saturation limit is not known however, until it is reached. Therefore, as mentioned above, the concentration must be increased mathematically by increments to predict what the saturation limit in an actual sterilization cycle would be over time under the desired conditions. The resulting concentrations of saturated hydrogen peroxide and water vapors are 10.4 mg/L and 51.0 mg/L, respectively. The final vapor composition at saturation calculates to be 0.097 mole fraction hydrogen peroxide (0.903 mole fraction water), or 16.9 wt% hydrogen peroxide.

Table I shows results of such calculations for specific cases of a sterilization cycle. All but a few of these cases are more complex than those of Table II. After 4.5 minutes in Table I, Vapor B contains hydrogen peroxide vapor as well as water mixture. Vapor A is still a 30 wt% hydrogen peroxide and water mixture. The hydrogen peroxide and water vapor concentrations of Vapor B continually change due to time-dependent degradation of hydrogen peroxide vapor and injections of vapor A. The saturation limit (column labeled "$H_2O_2$ satn, mg/L") change in accordance with changing hydrogen peroxide and water vapor concentrations in Vapor B ("$H_2O_2$, mg/L" and "Water, mg/L," respectively.

After 4.7 minutes in Table I injections of 30 wt% hydrogen peroxide vapor into an essentially vacant chamber at 4° C. reached the saturation limit of 0.49 mg vapor phase hydrogen peroxide per Liter. The saturation limit is the same as in Table II for 4° C. and 0% relative humidity.

After several periods of decomposition and make-up injections, at 9.86 minutes, the saturation limit is 0.17 mg vapor phase hydrogen peroxide per Liter. The vapor is no longer 0 wt%. Rather, it is only 4.7 wt% hydrogen peroxide (95.3 wt% water), or 0.025 mole fraction hydrogen peroxide. Interpolations of Table IV and of Table III (or iterative solution of the basic equations) provide the saturation limit of 0.17 mg/L.

The next entry in Table I, "inject" at 9.86 minutes, shows conditions immediately following instantaneous injection of 8 mg of 30 wt% hydrogen peroxide mixture. Hydrogen peroxide concentration increased by 0.05 mg/L, to 0.176. This is greater than the saturation limit prior to injection, yet the "Vapor % satn" column shows only 86.3% saturated. The saturation limit also increased, because the hydrogen peroxide mole fraction increased to 0.0333. Table IV indicates that 0.0333 mole fraction hydrogen peroxide at 4° C. corresponds to 0.4 mole fraction liquid, which corresponds to 3.11 torr saturation pressure in Table III. This leads, through use of the relationship $C = MYP/RT$ described previously, to the saturation limit of 0.20 mg/L hydrogen peroxide shown in Table I.

FIG. 4 illustrates the saw-tooth course of both the hydrogen peroxide vapor concentration and the saturation limit as decomposition periods and make-up injections alternate. Water vapor concentration increases with both decomposition and make-up injections, so as time progresses the saturation limit and the actual hydrogen peroxide vapor concentration get closer together. The size of further make-up injections would have to decrease to avoid saturation. Eventually, make-up injections could not be made without exceeding the saturation limit.

What is claimed is:

1. A sterilization method comprising:
   injecting a hydrogen peroxide and water vapor mixture into a closed sterilization chamber having a predetermined volume at a predetermined temperature in an initial amount approaching the saturation limit of said vapor mixture in said chamber at said temperature and said volume; and,
   thereafter, injecting a plurality of intermittent make-up injections of said vapor mixture into said chamber, said make-up injections being at a rate and each said make-up injection being in a variable amount necessary to maintain the concentration of hydrogen peroxide vapor at a level effective for sterilization but less than that concentration of hydrogen peroxide vapor which would raise the concentration of said vapor mixture to the saturation limit which will be present in said chamber immediately following injection of such make-up injection at said temperature.

2. The method of claim 1 wherein said hydrogen peroxide and water vapor mixture has a percent composition of 30% by weight.

3. The method of claim 1 wherein said temperature is about 4° C.

4. The method of claim 1 wherein said initial amount, each said variable amount and the saturation limits for said vapor mixture are predetermined.

5. The method of claim 1 wherein the saturation limits for said vapor mixture and each said variable amount are determined by continuously monitoring the relative humidity and the hydrogen peroxide vapor concentration within said chamber.

* * * * *

UNITED STATES PATENT AND TRADEMARK OFFICE
CERTIFICATE OF CORRECTION

PATENT NO. : 4,956,145

DATED : September 11, 1990

INVENTOR(S) : Arthur L. Cummings, Robert W. Childers and Thaddeus J. Mielnik

It is certified that error appears in the above-identified patent and that said Letters Patent is hereby corrected as shown below:

On the title page:

In the References Cited insert --4,863,688 9/89 Schmidt et al.--.

Col. 3, line 32, delete "(rorr)" and substitute therefor --(torr)--..

Col. 3, line 48, delete "(time = 4 5)" and substitute therefor --(time = 4.5)--.

Col. 7, line 14, delete "warer" and substitute therefor --water--.

Col. 7, line 15, delete "rhe" and substitute therefor --the--.

Col. 10, line 40, delete "ar" and substitute therefor --at--.

Col. 12, line 23, delete "0.815" and substitute therefor --0.815)--.

UNITED STATES PATENT AND TRADEMARK OFFICE
CERTIFICATE OF CORRECTION

PATENT NO. : 4,956,145

DATED : September 11, 1990

INVENTOR(S) : Arthur L. Cummings, Robert W. Childers and Thaddeus J. Mielnik

It is certified that error appears in the above-identified patent and that said Letters Patent is hereby corrected as shown below:

Col. 13, line 30, delete "0 wt. %." and substitute therefor -- 30 wt. %.--.

Signed and Sealed this

Sixteenth Day of June, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,956,145

DATED : September 11, 1990

INVENTOR(S) : Arthur L. Cummings, Robert W. Childers and Thaddeus J. Mielnik

It is certified that error appears in the above-identified patent and that said Letters Patent is hereby corrected as shown below:

ON TITLE PAGE:

In the Inventors insert --Thaddeus J. Mielnik--.

Signed and Sealed this

Seventh Day of July, 1992

Attest:

DOUGLAS B. COMER

Attesting Officer

Acting Commissioner of Patents and Trademarks